United States Patent
Hoshino et al.

[11] Patent Number: 5,906,998
[45] Date of Patent: May 25, 1999

[54] METHOD FOR DECOMPOSING POLYMER CONTAINING URETHANE LINKAGE AND/OR UREALINKAGE

[75] Inventors: Yuji Hoshino; Takaaki Masuda, both of Toyota; Hiroshi Ikuta; Hisao Mitobe, both of Amagasaki, all of Japan

[73] Assignees: Sumitomo Bayer Urethane Co., Inc., Hyogo-ken; Toyota Jidosha Kabushiki Kaisha, Aichi-ken, both of Japan

[21] Appl. No.: 08/702,499

[22] PCT Filed: Dec. 25, 1995

[86] PCT No.: PCT/JP95/02647

§ 371 Date: Aug. 20, 1996

§ 102(e) Date: Aug. 20, 1996

[87] PCT Pub. No.: WO96/20244

PCT Pub. Date: Jul. 4, 1996

[30] Foreign Application Priority Data

Dec. 27, 1994 [JP] Japan .................................. 6-324528

[51] Int. Cl.$^6$ ........................................................ C08J 11/10
[52] U.S. Cl. ........................... 521/49.5; 526/914; 560/26; 560/157; 560/345; 564/32; 564/335; 564/393; 564/414; 564/487
[58] Field of Search ........................... 521/49.5; 526/914; 560/345, 26, 157; 564/393, 335, 487, 414, 32

[56] References Cited

U.S. PATENT DOCUMENTS

| | | | |
|---|---|---|---|
| 3,404,103 | 10/1968 | Matsudaira et al. | 260/2.3 |
| 4,039,568 | 8/1977 | Sakai et al. | 260/453 P |
| 4,160,749 | 7/1979 | Schneider et al. | 260/2.3 |
| 4,281,197 | 7/1981 | Oblinger | 564/393 |

FOREIGN PATENT DOCUMENTS 537 579  4/1993  European Pat. Off. .

OTHER PUBLICATIONS

Database WPI GB: AN 83–46423k[19] & SU, A,940 035 (Kapapetyan O.O. ) Jul. 5, 1982 see abstract.

*Primary Examiner*—Shailendra Kumar
*Attorney, Agent, or Firm*—Joseph C. Gil; Lyndanne M. Whalen

[57] ABSTRACT

In the decomposition of a polymer containing a urethane linkage and/or urea linkage in the presence of a decomposing agent, the amount of evolved carbon dioxide is measured and the decomposition reaction is conducted until a total amount of evolved carbon dioxide reaches a specified value to obtain a liquid decomposition product. According to the present invention, a decomposition product having constant quality can be obtained in a simple manner.

6 Claims, No Drawings

METHOD FOR DECOMPOSING POLYMER CONTAINING URETHANE LINKAGE AND/OR UREALINKAGE this application is a 371 of PCT/JP95/02647, filed Dec. 25, 1995.

FIELD OF THE INVENTION

The present invention relates to a method for decomposing a polymer containing a urethane linkage and/or urea linkage.

RELATED ART

Along with increase of the amount of consumed polymers containing a urethane linkage and/or urea linkage in recent years, the disposal of the waste formed during their manufacturing and the waste formed after a product being sold in market has become a critical problem. One of the solutions for this problem is to liquify the waste by decomposition. After the decomposition, the waste may be incinerated efficiently or may be processed for recycling.

One of the methods for decomposing a polymer employs an amine or alcohol as a decomposing agent, an alkaline catalyst of an alkali metal or alkaline earth metal hydroxide has been used, and such method is disclosed in Japanese Patent Publication No. Showa 43-21079 (21079/1968) Japanese Patent Laid-Open Publication No. Showa 51-44179 (44179/1976) and the like. In this case, the fluctuation of reaction temperature, the fluctuation of composition of polymer and the contamination by impurities give a change of reaction rate so that it has been difficult to obtain a liquid decomposed product having a constant quality.

Consequently, after decomposition of a polymer containing a urethane linkage and/or urea linkage to a liquid, it has been reused as a raw material for making molded products of relatively low quality or in so a considerably low composition ratio that it does not give an undesired influence on the physical properties of molded products.

It is supposed, for example, that the change of the amine value in the decomposition product is monitored for obtaining a liquid decomposition product having a constant quality. However, the measurement of the amine value suffers from disadvantages of a relatively long time and a rather complicated procedure.

SUMMARY OF THE INVENTION

An object of the present invention is to provide a method for decomposing a polymer without such disadvantages, whereby a liquid decomposition product having a constant quality can be obtained from a polymer containing a urethane linkage and/or urea linkage.

The present invention relates to a method for decomposing a polymer containing a urethane linkage and/or urea linkage in the presence of a decomposing agent, comprising measuring an amount of evolved carbon dioxide and conducting a decomposing reaction until the total amount of evolved carbon dioxide reaches at least 60%, preferably at least 70% of a maximum evolved carbon dioxide amount to give a liquid decomposed material.

DETAILED DESCRIPTION OF THE INVENTION

When the total amount of evolved carbon dioxide reaches the specified value, the decomposition reaction is discontinued. Discontinuation of the decomposition reaction is performed by lowering reaction temperature or by separating the decomposing agent from the decomposition mixture.

When the decomposition is completely conducted, the total amount of evolved carbon dioxide reaches a maximum value. In the present invention, during the total amount of the evolved carbon dioxide changes from 0 to a maximum value (at which the amount of evolved carbon dioxide per unit time no longer increases), the decomposition reaction is discontinued at a stage when the decomposition product becomes liquid and has a quality suitable for recycling. Such stage is a time when the total amount of evolved carbon dioxide reaches usually at least 60%, preferably at least 70% of the maximum value.

The measurement of the amount of evolved carbon dioxide may be carried out by using a gas meter or by measuring the weight of an absorbent such as calcium oxide absorbing the evolved carbon dioxide.

The polymer containing the urethane linkage and/or urea linkage may be manufactured by adding and reacting an isocyanate compound to a compound containing active hydrogen in the presence of optionally a crosslinking agent, a catalyst, a foaming agent, a. stabilizer and other auxiliaries.

The isocyanate compound is a polyisocyanate, for example, an aromatic polyisocyanate such as tolylene diisocyanate, diphenylmethane diisocyanate and polymethylene polyphenyl polyisocyanate; an aliphatic polyisocyanate such as hexamethylene diisocyanate; a modified polyisocyanate, for example, urethane-modified, carbodiimide-modified, allophanate-modified, urea-modified and biuret-modified polyisocyanate; and an isocyanate prepolymer.

Examples of the compound containing active hydrogen are a polyether polyol, a polymeric polyol, a polyester polyol and a polyether polyamine. The molecular weight of the compound containing active hydrogen is in the range from 400 to 20,000.

Examples of the crosslinking agent are a glycol compound, for example, ethylene glycol, diethylene glycol, 1,4-butanediol, 1,3-butanediol, propylene glycol and dipropylene glycol; and an amine compound, for example, diethyltolylene diamine, t-butyltolylene diamine, N,N,N',N'-tetramethyl-diaminodiphenylmethane, ethanolamine, diethanolamine, triethanolamine, ethylene diamine and diethylene triamine. The molecular weight of the crosslinking agent in the range from 60 to 400.

As the decomposing agent is employed an alcohol and/or amine.

The amine which can be used as the decomposing agent is an aliphatic amine, an aromatic amine, an alicyclic amine or an alkanolamine. Examples are butylamine, hexylamine, dibutylamine, tributylamine, ethylenediamine, tetramethylenediamine, hexamethylenediamine, diethylenetriamine, 2-(2aminoethoxy)ethanol, ethanolamine, diethanolamine, triethanolamine, polyoxypropylene polyamine, aniline, N-methylaniline, o-toluidine, m-toluidine, p-toluidine, 1-methyl-3,5-diethyl-2,6-diaminobenzene,1-methyl-3-t-butyl-2,4-diaminobenzene,1-methyl-3-t-butyl-2,6-diaminobenzene,4,4'-diaminodiphenylmethane, cyclohexylamine, piperazine and piperidine.

The alcohol which can be used as the decomposing agent is a monovalent or polyvalent alcohol or an alkyleneoxide adduct of an alcohol. Examples of such alcohol are methanol, ethanol, butanol, hexanol, ethylene glycol, propylene glycol, 1,4-butanediol, 1,3-butanediol, glycerol, trimethylolpropane, polyoxyethylene glycol and polyoxypropylene glycol. Examples of the alkyleneoxide are ethyleneoxide, propyleneoxide and butyleneoxide.

The amount of the alcohol and/or amine used as the decomposing agent is from 10 to 300 parts by weight per 100 parts by weight of the polymer containing the urethane linkage and/or urea linkage. More than 300 parts by weight, for example 1,000 parts by weight, of the alcohol and/or amine can be used, but this is not preferable, since this has an inferior efficiency in that the polymer to be treated at once has a relatively smaller amount.

The polymer is generally a solid. The solid polymer to be applied to the decomposition reaction preferably has a size of from about 0.01 cm to about 5 cm. The solid polymer can have such a size by the cutting, the grinding and the like. The decomposition temperature is from 100 to 300° C. The pressure applied for the decomposition is from an ordinary pressure to 200 kg/cm$^2$. After the decomposition reaction, a part or all of excess decomposing agent, namely the alcohol and/or amine, may be removed by distillation or by other techniques.

In the method of the present invention, the polymer is decomposed to give a liquid decomposition product.

The liquid decomposition product has a viscosity of 10 to 1,000,000 cps/25° C. The polymer containing the urethane linkage and/or urea linkage is decomposed to give a monomer or a polymer having lower molecular weight. The polymer having lower molecular weight contains the active hydrogen. The group which contains active hydrogen is, for example, an amino or hydroxyl group. The polymer having low molecular weight may contain a urethane linkage and/or urea linkage.

According to the present invention, a liquid decomposition product having a constant quality, for example a constant amine value, can be obtained in a simple manner.

PREFERRED EMBODIMENTS OF THE INVENTION

Below are shown Examples and Comparative Examples for explanation of the present invention in more detail. The present invention is not limited to the following Examples.

Components and equipments employed in the following Examples and Comparative examples are as follows:
(1) Waste Polyurethane/Urea Chip To a liquid prepared by formulating 80 pbw of polyol A, 18 pbw of polyamine A, 2 pbw of crosslinking agent A, 0.1 pbw of catalyst A and 0.05 pbw of catalyst B, was added polyisocyanate A at an isocyanate index of 107 to give a urethane/urea polymer having a density of 1.03 g/cm$^3$, a flexural modulus of 3,000 kg/cm$^2$, a tensile strength of 250 kg/cm$^2$, an elongation at break of 230% and a heat sag (at 120° C. for 1 hour, 100 mm overhang) of 5 mm by a reaction injection molding process. This polymer was granulated to chips having particle diameter of 2–5 mm by using a grinder.
Polyol A
Polyether polyol having a hydroxyl value of 28 mg KOH/g which is prepared by adding propylene oxide to glycerol.
Polyamine A
A mixture of 3,5-diethyl-2,4-diaminotoluene and 3,5-diethyl-2,6-diaminotoluene.
Crosslinking agent A
Polyether polyol having an average molecular weight of 356 and a hydroxyl value of 630 mg KOH/g which is prepared by adding propylene oxide to ethylenediamine.
Catalyst A
Dibutyltin dilaurate.
Catalyst B
33% solution of triethylenediamine in dipropylene glycol.
Polyisocyanate A
Urethane-modified diphenylmethane diisocyanate (content of isocyanate group: 23%).

(2) Decomposing Agent Ethylene glycol.
(3) Equipments
A 500 L stainless steel reactor equipped with an agitator.
A heat exchanger for condensation of the decomposing agent having a heat exchange area of 2 m$^2$.
A dry-type gas meter, a product of Shinagawa Seiki K.K.

EXAMPLE 1

200 kg of a waste polyurethane/urea chip and 200 kg of a decomposing agent were charged in a reactor and the reaction was conducted by heating to 190° C. During the reaction, carbon dioxide evolved. A mixture gas of vaporized decomposing agent and carbon dioxide was introduced into a heat exchanger and the decomposing agent was condensed and returned into the reactor while carbon dioxide was introduced into a gas meter for the measurement of the volume of evolved carbon dioxide. The cumulative volume of evolved carbon dioxide was observed. When it reached 6.5 m$^3$ (a value under a standard condition), the reaction was discontinued by lowering the reaction temperature to 100° C. The reaction time was 9 hours. The decomposition product had an amine value of 92 mg KOH/g.

EXAMPLE 2

Except that the reaction temperature was 195° C., the same procedure as in Example 1 was repeated. The cumulative volume of evolved carbon dioxide was 6.5 cm$^3$ and the reaction time was 6.5 hours. The decomposition product had an amine value of 93 mg KOH/g.

COMPARATIVE EXAMPLE 1

Without the use of a gas meter, the reaction was conducted at 190° C. for 6 hours. The decomposition product had an amine value of 74 mg KOH/g.

COMPARATIVE EXAMPLE 2 without the use of a gas meter, the reaction was conducted at 195° C. for 6 hours. The decomposition product had an amine value of 88 mg KOH/g.

We claim:
1. A method for decomposing a polymer containing a urethane linkage and/or urea linkage in the presence of a decomposing agent, comprising measuring an amount of evolved carbon dioxide and conducting a decomposing reaction until the total amount of evolved carbon dioxide reaches at least 60% of a maximum evolved carbon dioxideount to give a liquid decomposed material.

2. The method according to claim 1, wherein the amount of evolved carbon dioxide is measured by using a gas meter.

3. The method according to claim 1, wherein the amount of evolved carbon dioxide is measured by measuring the weight of an absorbent absorbing the evolved carbon dioxide.

4. The method according to claim 1, wherein the decomposing agent is an alcohol or amine.

5. The method according to claim 1, wherein the amount of the decomposing agent is from 10 to 300 parts by weight per 100 parts by weight of the polymer containing the urethane linkage and/or urea linkage.

6. The method according to claim 1, wherein the decomposition reaction is conducted at a temperature of from 100 to 300° C.

* * * * *